(12) United States Patent
Hexsel

(10) Patent No.: US 10,744,135 B2
(45) Date of Patent: Aug. 18, 2020

(54) USE OF AN ACTIVE SUBSTANCE IN THE TREATMENT OF MELASMA

(71) Applicant: Doris Maria Hexsel, Porto Alegre (BR)

(72) Inventor: Doris Maria Hexsel, Porto Alegre (BR)

( * ) Notice: Subject to any disclaimer, the term of this patent is extended or adjusted under 35 U.S.C. 154(b) by 0 days.

(21) Appl. No.: 16/313,526

(22) PCT Filed: Jun. 28, 2017

(86) PCT No.: PCT/BR2017/050167
§ 371 (c)(1),
(2) Date: Apr. 2, 2019

(87) PCT Pub. No.: WO2018/000067
PCT Pub. Date: Jan. 4, 2018

(65) Prior Publication Data
US 2019/0269680 A1    Sep. 5, 2019

(30) Foreign Application Priority Data

Jun. 28, 2016 (BR) .............................. 102016015213
Feb. 24, 2017 (BR) .............................. 132017003992

(51) Int. Cl.
| | | |
|---|---|---|
| *A61K 31/498* | (2006.01) |
| *A61K 9/00* | (2006.01) |
| *A61K 8/02* | (2006.01) |
| *A61K 8/04* | (2006.01) |
| *A61K 8/49* | (2006.01) |
| *A61P 7/00* | (2006.01) |
| *A61Q 17/04* | (2006.01) |
| *A61P 17/00* | (2006.01) |
| *A61K 45/06* | (2006.01) |

(52) U.S. Cl.
CPC ............ *A61K 31/498* (2013.01); *A61K 8/022* (2013.01); *A61K 8/042* (2013.01); *A61K 8/494* (2013.01); *A61K 9/0014* (2013.01); *A61P 17/00* (2018.01); *A61Q 17/04* (2013.01); *A61K 45/06* (2013.01); *A61K 2800/10* (2013.01); *A61K 2800/43* (2013.01)

(58) Field of Classification Search
CPC .......... A61K 31/498; A61K 9/00; A61K 8/02; A61K 8/04; A61K 8/49; A61P 7/00; A61Q 17/04
See application file for complete search history.

(56) References Cited

U.S. PATENT DOCUMENTS

2012/0082625 A1* 4/2012 Graeber ............... A61K 9/0014
424/43
2014/0113947 A1* 4/2014 Shanler ................. A61K 47/14
514/400

* cited by examiner

*Primary Examiner* — Zohreh A Fay
(74) *Attorney, Agent, or Firm* — Lambert Shortell & Connaughton; Gary E. Lambert; David J. Connaughton, Jr.

(57) ABSTRACT

The present invention belongs, in a general manner to the technological field of the pharmaceutical industry and relates, more specifically, to one or more compositions of second use to be destined for the treatment of melasma. The present invention relates to the use of substances belonging to the group of alpha-adrenergic receptor agonists, in different variable concentrations, for treating conditions of melasma upon human skin. Furthermore, the present invention discloses pharmaceutical compositions, the latter being associated or not with other compounds or methods of treatment, to be utilised for the treatment of melasma.

9 Claims, 2 Drawing Sheets

[Fig. 1]
[Fig. 2]
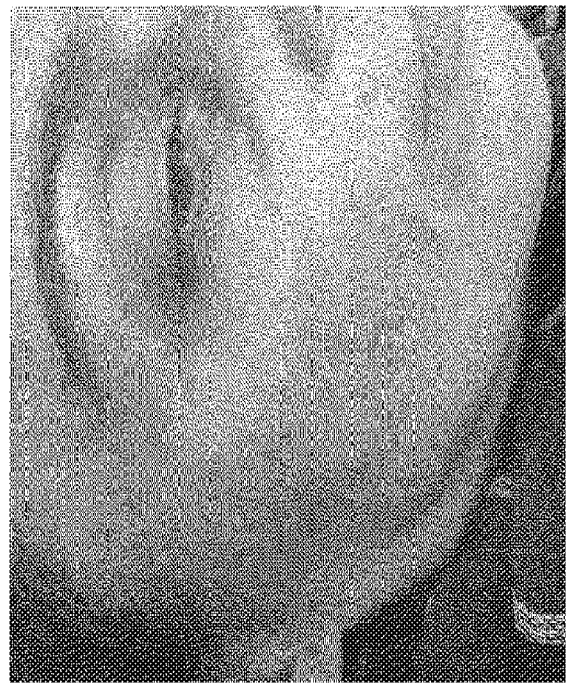

[Fig. 3]
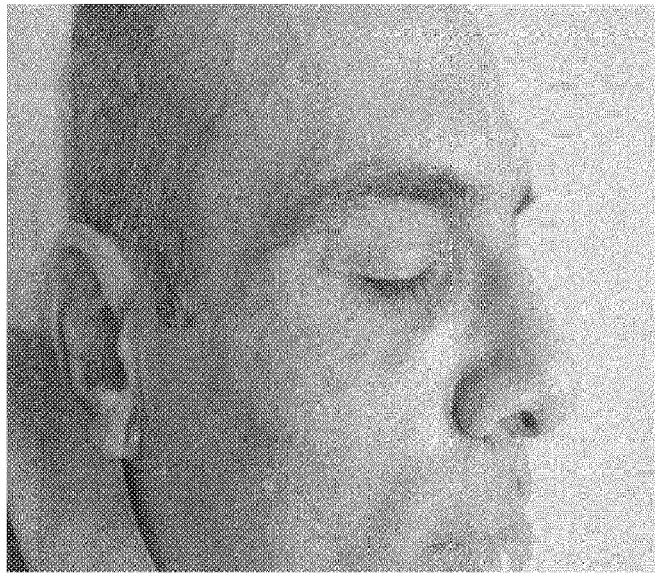
[Fig. 4]

USE OF AN ACTIVE SUBSTANCE IN THE TREATMENT OF MELASMA

CROSS-REFERENCE TO RELATED APPLICATIONS

The present application claims priority to PCT Patent Application No. PCT/BR2017/050167 filed on Jun. 28, 2017 which claims to priority to Brazilian Patent Application No. BR 13 2017 003992-6 filed on Feb. 24, 2017 and Brazilian Patent Application No. BR 10 2016 015213-5 filed on Jun. 28, 2016, the disclosures of which is incorporated herein by reference.

STATEMENT RE: FEDERALLY SPONSORED RESEARCH/DEVELOPMENT

Not Applicable

BACKGROUND

Technological Field of the Invention

The present invention belongs, in a general manner, to the technological field of the pharmaceutical industry and relates, more specifically, to one or more compositions of second use to be destined for the treatment of melasma.

BRIEF SUMMARY

State of the Art

Melasma is a very-common dermatological condition characterised by brown patches on the skin, principally affecting the face. The patches are typically upon the forehead, cheeks, upper lip, chin and the nose, and may furthermore affect areas other than the face, such as the neck, the back and the arms.

Melasma is a very-common dermatological disorder. The incidence thereof varies in different populations, it being estimated at between 1.5% and 33% according to studies published by Pichardo et al [Pichardo R, Vallejos Q, Feldman S R, Schulz M R, Verma A, Quandt S A, et al. *The prevalence of melasma and its association with quality of life in adult male Latino migrant workers. Int J Dermatol.* 2009; 48:22-6] and by Werlinger et al [Werlinger K D, Guevara I L, González C M, Rincón E T, Caetano R, Haley R W, et al. *Prevalence of self-diagnosed melasma among premenopausal Latino women in Dallas and Fort Worth, Tex. Arch Dermatol.* 2007; 143:424-5]. Such condition affects, principally, women of fertile age and impacts all ethnic groups, being more evident in dark-skinned persons. Cases of melasma classified as telangiectatic are rarely observed in men. The cause is unknown, however it is known that various factors are involved, such as those of a genetic, environmental (exposure to sunlight, to visible light—lamps—and to artificial tanning), hormonal (such as pregnancy, use of contraceptives and other hormonal changes) nature, together with the use of some medicaments and cosmetics potentially causing sun sensitisation. The factor considered most important in the development and aggravation of melasma is exposure to sunlight. Other than these factors, genetic predisposition and a positive family history are also related to the emergence of melasma.

The term 'telangiectatic melasma' is employed to characterise a type of melasma wherein telangiectasias are visible in the pigmented lesions of the melasma, both clinically and by dermatoscope, a non-invasive apparatus magnifying the image of the skin by approximately 10 times. Telangiectasias are commonly found in a large number of melasma lesions. A research study by Kim et al demonstrated robust evidence establishing the vascular theory of melasma and relating the pigmentation events to increased angiogenesis. These authors demonstrated that there is an increase in both number and size of the dermal vessels in melasma lesions compared to those of the adjacent normal skin. The vessels stimulate previously-identified specific factors resulting in an increase in melanogenesis, responsible for the increase in the pigmentation of the lesions.

Currently, dermatology disposes of various treatments for melasma. In all cases the most important measure is protection from sunlight. Diverse lightening or depigmenting agents of topical application are indicated to lighten the lesions of melasma. Hydroquinone is considered to be the gold-standard depigmenter. Other depigmentation agents include kojic acid, azelaic acid, arbutin and ascorbic acid. Recently, other agents have demonstrated depigmentation activities, inter alia tranexamic acid, rucinol, silymarin oligopeptides, various botanic extracts, including extracts from seeds of grape, pycnogenol, silymarin oligopeptides, green tea, aloesin, coffee berry, soya, extract of liquorice and of orchid. Among the most-used procedures are surface peels, crystal peels, fractionated lasers and microneedling, they being employable in combination with clinical treatments. The use of corrective cosmetics and sunscreens associated with corrective bases is useful in the treatment of melasma by virtue of the fact that they combine the advantages of partially concealing the lesions and, at the same time, protecting them from the sun.

Clinical studies demonstrate that the diverse treatments may ameliorate this dermatological condition to variable degrees, nevertheless up to the present there is no cure for melasma and it is difficult for all the lesions to be lightened. The recurrent aspect of this condition affects the quality-of-life of bearers thereof. In this sense, it is established that melasma lacks successful treatments or those which may act to ensure a better result than the existing treatments.

The aforementioned study by Kim et al detailed the vascular characteristics of melasma [Kim E H, Kim Y C, Lee E S, Kang H Y. *The vascular characteristics of melasma. J Dermatol Sci.* 2007; 46:111-6]. They found an increased endothelial growth factor in the skin affected by melasma, resulting in an increase in vascularisation. This presents a clinical implication in the increase in the pigmentation of lesions and, for this reason, the necessity exists to develop treatments, the target whereof is the vascular component of the melasma, without increasing the pigmentation. Another study carried out by Lee et al found an increased incidence of melanin, erythema and hydration in the lesions of melasma when compared with the adjacent perilesional normal skin. According to these authors, this proves that conspicuous vascularisation accompanies the hyperpigmentation [Lee D J, Lee J, Ha J, Park K C, Ortonne J P, Kang H Y. *Defective barrier function in melasma skin. J Eur Acad Dermatol Venereol.* 2012; 26:1533-7]. A prospective randomised split-face study carried out by Passeron et al demonstrated that association of the clinical treatment with triple combination cream (TCC: Triluma®) and pulsed-dye laser (PDL) was more effective than the TCC cream alone. This treatment was capable of preventing relapses of the disorder [Passeron T, Fontas E, Kang H Y, Bahadoran P, Lacour J P, Ortonne J P. *Melasma treatment with pulsed-dye laser and triple combination cream: A prospective, randomized, single-blind, split face study. Arch Dermatol.* 2011;

147:1106-8]. The TCC possesses a potent retinoid which may cause a collateral effect of increasing telangiectasias in the patches. Lasers and pulsed light, which could treat the telangiectasias of the melasma, are not routinely utilised because they generally cause an increase in pigmentation.

In this respect, a medicament capable of reducing the vessels without increasing pigmentation becomes an significant adjuvant for treating this important factor, reducing the hyperpigmentation of lesions. Minimising the vascular action, the stimulus towards melanogenesis is reduced, improving the melasma.

Among the procedures and topical products for treatment and/or amelioration of the symptoms of patients presenting melasma there may be cited methods and/or pharmaceutical formulations, being objects of patents and seeking alternatives for the symptoms of the dermatological condition in question. Patent document PI0311154-7 'Composition to improve melasma and composition to reduce the opacity of skin', describes a composition to ameliorate melasma comprising a purine substance (in short, nitrogenated bases consisting of heterocyclic organic compounds) related to nucleic acid and a pharmaceutically- or cosmetically-acceptable carrier presenting effects in the amelioration of the condition of melasma, by virtue of the action of the purine substance related to nucleic acid. However this solution does not act with a view to diminishing the vascularisation in the region of the melasma in the patient, it solely confers upon the composition properties to opacify the region, without effectively treating the lesions.

Another alternative consists of patent no. PI 0302225-0, 'Application for aromatase inhibitors or estradiol receptor blockers and derivatives thereof in the treatment of chloasma and melasma in human beings', disclosing a product for use in the treatment of patches identified as being of chloasma and melasma, comprising a formulation based on aromatase P450 inhibitors and total or partial estrogen receptor blockers. In summary, the invention discloses alpha-arbutin aromatase P450 inhibitors, phosphatidylcholine, ethanol, propylene glycol and polyacrylate gel. The composition may also comprise the use of chrisine and apigenin being isoflavones. The product has a carrier in the topical form and may present diverse consistencies. In spite of being intended for the treatment of melasma, knowing that the hormone receptors may be directly involved in such condition, the actuation of these aromatase inhibitors or estradiol receptor blockers lacks scientific evidence proving their actual efficacy upon the patches, in addition to not acting directly in the diminishment of the blood vessels.

U.S. Pat. No. 9,351,922, 'Composition for correcting skin pigment conditions', discloses a composition for treating conditions of pigmentation of human skin. The composition disclosed in the present patent application is provided with vegetable extracts (of glabra glycyrrhiza, of green tea, of pomegranate and of cucumber) associated with chemical compounds. Among such chemical compounds may be cited zinc oxide, ascorbic acid, alpha-arbutin, niacinamide and an acceptable carrier. The composition may be used to treat a variety of pigmentation problems, including melanoma, liver spots, melasma, post-inflammatory pigment issues, sun spots, freckles and age spots, nevertheless, in the same manner as in the other solutions cited, it does not act on the diminishment of the blood vessels in the area of the melasma.

U.S. Pat. No. 9,333,172, 'Topical skin care composition', discloses a process of obtainment of an emulsion for topical use for the treatment of conditions of skin pigmentation. The process basically provides the utilisation of fluocinolone acetonide, hydroquinone and tretinoin. One of the major disadvantages of the emulsion disclosed in this invention consists of the utilisation of a potent topical corticoid, the chronic use whereof may increase telangiectasias in the face, including those of melasma.

Another composition may be observed in U.S. Pat. No. 9,079,047, 'Cosmetic composition for skin whitening', disclosing a composition for lightening the skin containing at least two selected groups consisting of Magnolia obovata bark extracts, a Citrus unshiu peel extract, a wild soybean extract, a Ginkgo biloba leaf extract, and a honeysuckle extract. However, said composition solely acts superficially in the lightening of the pigmented patches without participating in the diminishment of vascularisation.

U.S. patent US2013295080, 'Pharmaceutical composition for treating melasma and preparation method thereof', also discloses a composition for treating conditions of pigmentation of the skin, preferentially of melasmas. The pharmaceutical composition is prepared based upon ginseng, salvia, mint, orange peel, peony, poria, liquorice, peach seeds, yam, Penthorum chinense, and a fermentation conversion solution of fruits and vegetables. A method of preparation of the pharmaceutical composition is also disclosed, however this alternative also is not characterised by acting upon the diminishment of blood vessels in the region affected by the telangiectatic melasma.

On the basis of the compositions and products currently available in general in the state of the art it is emphasised that in the market there does not exist a composition destined to minimise the vascular component of melasma, an important factor in this dermatological pathology, nor one employing brimonidine or other substances belonging to the group of alpha-adrenergic receptor agonists, for the treatment of the skin condition denominated melasma.

As presented above, it may be observed that the existing treatments for melasma are diverse, the majority being destined to depigment or lighten the lesions. This having been said, it is possible to conclude that the greatest disadvantages of the currently-known compositions in the market consist of the fact of their not presenting relevant treatment results. Finally, it is important to emphasise that among all the currently-known topical treatments, none thereof presuppose the use of brimonidine or other substances belonging to the pharmacological group of alpha-adrenergic receptor agonists in the composition thereof, generating visually-satisfactory results in the treatment of the condition of melasma by minimising a component recognised as presenting relevant participation in patches of melasma, the vascular component.

Novelties and Objectives of the Invention

The present invention relates to new compositions composed of substances of the pharmacological group of alpha-adrenergic receptor agonists, exemplified by, however not limited thereto, brimonidine in different concentrations ranging from 0.10% to 0.50%, for the treatment of conditions of melasma upon the human skin. Furthermore, the present invention discloses pharmaceutical compositions, which may or may not be associated with other compounds or methods of treatment, to be utilised in the treatment of melasma.

The application of topical products containing brimonidine exclusively, or other substances of the pharmacological group of alpha-adrenergic receptor agonists, in isolation or in association with other compounds, products or procedures, results in a significant improvement in hyperpigmented patches of melasma, acting upon the increased levels of telangiectasias found in the lesions and, as a consequence, accelerating or optimising the depigmentation effects of other treatments. In this manner, once a patient has been subjected to a topical treatment comprising the use of brimonidine, a favourable result may be verified in the reduction of the patches characteristic of the condition of telangiectatic melasma.

Topical brimonidine is an alpha-adrenergic agonist, utilised initially to reduce intraocular pressure in patients presenting glaucoma or ocular hypertension. The development of medicaments destined for the constriction of blood vessels is important to provide evidence for an improvement in the conditions causing erythema upon the skin of patients. By virtue of the fact that brimonidine is an alpha-adrenergic agent, the use of compositions containing this active substance is shown to be an effective alternative for the vascular component of melasma responsible for increasing the pigmentation of patches of this condition.

Upon the basis of the use of treatments comprising brimonidine it may be verified that, when applied in the morning, the effects thereof in minimising the deterioration brought about by sunlight are effective for up to 9 hours, boosting in this manner the action of other depigmenters used in the treatment of melasma, particularly of the telangiectatic variant.

Additionally, it is observed that the use of an alpha-adrenergic agonist for the treatment of melasma results in satisfactory effects in terms of the hyperpigmentation of the skin in these conditions. Furthermore, it is important to state that the action of these compounds in the constriction of blood vessels consists in an effect not generally achieved with other currently-known means of treatment.

BRIEF DESCRIPTION OF THE DRAWINGS
DESCRIPTION OF THE APPENDED DRAWINGS

Having the objective of providing figures to illustrate the action of the use of the composition disclosed in the present application for a patent of invention, and in order that the solution may be fully understood and put into practice by any technical person in this technological field, it will be described in a clear, concise and adequate manner, taking as a basis the photographs appended, illustrating and supporting it, listed below:

FIG. 1 shows the area of the skin of the patient to be treated with a composition disclosed in the present document, in this case the use of an alpha-adrenergic agonist, prior to the application of the medicament upon a patient of the female sex.

FIG. 2 shows the area of the skin of the patient to be treated with the composition disclosed in the present document subsequent to the application of the medicament upon a patient of the female sex.

FIG. 3 shows the area of the skin of the patient to be treated with a composition disclosed in the present document, in this case the use of an alpha-adrenergic agonist, prior to the application of the medicament upon a patient of the male sex.

FIG. 4 shows the area of the skin of the patient to be treated with the aforementioned composition subsequent to the application of the medicament upon a patient of the male sex.

DETAILED DESCRIPTION OF THE INVENTION

The present invention discloses the use of pharmaceutical compositions presenting efficacity in the treatment of melasma through reduction of the vascularisation of the lesions. The improvement in the appearance of the patches occurs once the compositions herein disclosed minimise the action of the vessels in the increase of pigmentation and boost the action of the depigmenting medicaments.

Melasma consists in the appearance of dark patches of brown colour, it being a disorder considered to be incurable and of chronic and recurrent progression. It is important to emphasise that in the variant of melasma referred to as telangiectatic, the increased telangiectasias in this cutaneous condition are, according to medical publications, directly involved in the hyperpigmentation and tend to be chronic, lacking effective treatments which do not worsen the primary condition. The vessels customarily increase with the passage of time, without reversion of this condition, this not customarily being the case with the current indications of brimonidine which may be currently associated with and utilised for cases of acute erythema, such that of rosacea.

The composition in question is constituted by an active substance of the group of alpha-adrenergic receptor agonists and a pharmaceutically-acceptable carrier q.s., which may be both a medicament or a cosmetic. Consequently, the present invention discloses the topical use of the active substance brimonidine (or other drug belonging to the same alpha-adrenergic agonist group) at from 0.10% to 0.50%, in therapeutic concentrations, having the objective of acting such as to result in the reduction of melasmas. By virtue of it being an alpha-adrenergic agent, it is possible to verify the action of the composition directly upon blood pressure and, consequently, the actuation thereof upon the blood vessels irrigating the melasmas. The composition in question is, thus, applied upon the skin having lesions of melasma which may or may not present a clinically- or dermatoscopically-evident vascular component.

In this manner, the topical composition containing the active principle may also be associated with other compounds having the purpose of preventing, treating or occulting the pigmentation of melasma, such as sunscreens, depigmenters and corrective bases. In this case the active substance may be associated with depigmenting compounds or with other compounds destined to protect the skin, such as sunscreens or, furthermore, compounds destined to a occult the patches of melasma, such as the case of BB and CC creams, screens with a base or corrective bases.

All superficial topical treatments currently utilised for remediation of conditions of melasma may have added thereto substances of the pharmacological category of alpha-adrenergic receptor agonists in order to achieve satisfactory effects. For example, compositions containing brimonidine in concentrations from 0.10% to 0.50% may be applied prior to and following the application different surface peels.

In this manner, having the objective of supplying a range of products acting in the prevention and/or remediation of hyperpigmentations of skin affected by melasma, the present invention discloses the addition of the active substance of the alpha-adrenergic receptor agonist group, preferentially brimonidine, in concentrations from 0.10% to 0.50%, to the cosmetic composition containing corrective bases, sunscreens and bleaching compounds. Therapeutic quantities of brimonidine associated with these compositions may ensure an improved therapeutic effect over sunscreens and bleaching compounds and better cover of the lesions by the corrective bases. In order to render this invention clear the same is illustrated by the examples presented below.

Example 1: in one alternative of treatment of conditions of melasma, brimonidine in concentrations from 0.10% to 0.50% is associated with a pharmaceutically-acceptable carrier q.s. This composition must be applied to the skin over the patches of melasma in the form of powders, bases, creams, lotions, gels or other pharmaceutical presentations.

Example 2: in a second type of application, brimonidine in concentrations from 0.10% to 0.50% is associated with sunscreens, the stability of the formulation being tested.

Example 3: in a third example of composition, brimonidine in concentrations from 0.10% to 0.50% must be associated with depigmenter agents. In this manner, the action of the active principle brimonidine must be as a booster means, by virtue of the fact that it acts directly upon the blood vessels, thus reducing the hyperpigmentation of the areas of lesions of melasma.

Example 4: in a fourth medium of application, brimonidine is added to compounds destined to occult the imperfections of the skin, such as is the case of BB and CC creams, screens with a base or corrective bases. In this case brimonidine must be added to the cosmetics in concentrations from 0.10% to 0.50%.

Example 5: brimonidine in concentrations from 0.10% to 0.50% may, finally, be utilised in aesthetic treatments in a general manner as an application prior to surface peels or, more specifically, crystal and diamond peels.

FIGS. 1 to 4 appended to the present patent application demonstrate the efficacy of the application of the use of compositions containing the active principle brimonidine upon patients presenting telangiectatic melasma. FIG. 1 shows the area selected for application of a product containing the alpha-adrenergic agonist brimonidine upon the skin of the lesions of melasma; this figure shows the area prior to the application. FIG. 2 shows the area wherein the application of the composition disclosed occurred, there being an effective improvement in the hyperpigmentation of the skin of the melasma lesions minutes following the application of the medicament upon a patient of the female sex. FIGS. 3 and 4 show a patient of the male sex subjected to the same circumstances. It is emphasised that the effects of this medicament customarily increase gradually over periods of from 1 to 3 hours, calculated from the application of the composition upon the skin. Furthermore, the effects of the composition diminish after 6 to 9 hours following application upon the skin. As is known, the increase in pigmentation occurs to a greater extent during the day, wherein the action of the light is an important causal factor. Consequently, it is recommended that application of the products containing the active principle brimonidine be made in the morning or up to 6 hours prior to the patient being exposed to visible light or solar radiation, in order that the effects thereof be benefited from better. It can be verified that the application of this product upon lesions of telangiectatic melasma results in immediate and obvious improvement of the lesions of this type of skin condition following a period of 30 to 60 minutes from application.

In this manner, in addition to brimonidine, there are furthermore disclosed other examples of substances belonging to the group of alpha-adrenergic receptor agonists utilisable in an analogous manner, however not limited thereto: apraclonidine, clonidine, desglymidodrine, dexmedetomidine, dopamine, ephedrine, epinephrine, epinine (N-methyldopamine), ethylnorepinephrine, phenylephrine, phenylpropanolamine, guanabenz, guanfacine, 1-dobutamine, levarterenol, lofexidine, mephentermine, metaraminol, methylphenidate, methoxamine, midodrine, mitodrine, mivazerol, moxonidine, naphazoline, norepinephrine, norphenylephrine, oxymetazoline, pemoline propylhexedrine, propylhexedrine, tetryzoline, tizanidine, xylometazoline, α-methyldopa, α-methylnorepinephrine, (4,5-dihydro-1H-imidazol-2-yl)-(8-methyl-quinoxalin-6-yl)-amine, (4,5-dihydro-1H-imidazol-2-yl)-quinoxalin-5-yl-amine, (5-bromo-2-methoxyquinoxalin-6-yl)-(4,5-dihydro-1H-imidazol-2-yl)-amine, (5-bromo-3-methylquinoxalin-6-yl)-(4,5-dihydro-1H-imidazol-2-yl)-amine, (8-bromoquinoxalin-5-yl)-(4,5-dihydro-1H-imidazol-2-yl)-amine, (8-bromoquinoxalin-6-yl)-(4,5-dihydro-1H-imidazol-2-yl)-amine.

This descriptive memorandum has revealed dermatological compositions for topical use containing an alpha-adrenergic agonist (brimonidine or other drug of the same pharmacological group of alpha-adrenergic agonists) destined for the treatment of melasma, being marked by novelty, inventive activity, descriptive and comprobatory adequacy, industrial application and, consequently, presenting all the essential requisites for the grant of the privilege wherefore application is made.

The invention claimed is:

1. A method of Use of a pharmaceutical composition comprising an active substance of the group of alpha-adrenergic receptor agonists, comprising the step of applying the composition to a skin lesions of melasma.

2. The method of use the pharmaceutical composition comprising an active substance of the group of alpha-adrenergic receptor agonists according to claim 1, furthermore characterized in that the active substance of the group of alpha-adrenergic receptor agonists is brimonidine.

3. The method of use the pharmaceutical composition comprising an active substance of the group of alpha-adrenergic receptor agonists according to claim 2, furthermore characterized in that the active substance brimonidine is present in concentrations ranging from 0.10% to 0.50%.

4. The method of use the pharmaceutical composition comprising an active substance of the group of alpha-adrenergic receptor agonists according to claim 3, furthermore characterized in that the active substance brimonidine is present in a specific concentration of 0.33%.

5. The method of use the pharmaceutical composition comprising an active substance of the group of alpha-adrenergic receptor agonists according to claim 2, furthermore characterized in that the active substance of the group of alpha-adrenergic receptor agonists further comprises at least one of a compound selected from the group consisting of: apraclonidine, clonidine, desglymidodrine, dexmedetomidine, dopamine, ephedrine, epinephrine, epinine (N-methyldopamine), ethylnorepinephrine, phenylephrine, phenylpropanolamine, guanabenz, guanfacine, 1-dobutamine, levarterenol, lofexidine, mephentermine, metaraminol, methylphenidate, methoxamine, midodrine, mitodrine, mivazerol, moxonidine, naphazoline, norepinephrine, norphenylephrine, oxymetazoline, pemoline propylhexedrine, propylhexedrine, tetryzoline.

6. The method of use the pharmaceutical composition comprising an active substance of the group of alpha-adrenergic receptor agonists according to claim 2, furthermore characterized in that the active substance brimonidine is associated with other therapeutic compounds.

7. The method of use the pharmaceutical composition comprising an active substance of the group of alpha-adrenergic receptor agonists according to claim 2, furthermore characterized in that the active substance brimonidine is associated with other cosmetic compounds.

8. The method of use the pharmaceutical composition comprising an active substance of the group of alpha-adrenergic receptor agonists according to claim 6, furthermore characterized in that the active substance brimonidine is associated with peeling procedures in the treatment of melasma.

9. The method of use the pharmaceutical composition comprising an active substance of the group of alpha-adrenergic receptor agonists according to claim 7, furthermore characterized in that the active substance brimonidine is associated with bleaching compounds, corrective cosmetics and/or sunscreens.

\* \* \* \* \*